US00PP15890P3

(12) United States Plant Patent
vanSanden

(10) Patent No.: US PP15,890 P3
(45) Date of Patent: Jul. 26, 2005

(54) *LAMIUM MACULATUM* 'PURPLE DRAGON'

(50) Latin Name: *Lamium maculatum*
Varietal Denomination: Purple Dragon

(76) Inventor: John vanSanden, 4107 Orshal Rd., Whitehall, MI (US) 49417

( * ) Notice: Subject to any disclaimer, the term of this patent is extended or adjusted under 35 U.S.C. 154(b) by 100 days.

(21) Appl. No.: 10/061,483

(22) Filed: Feb. 4, 2002

(65) Prior Publication Data

US 2003/0150032 P1 Aug. 7, 2003

(51) Int. Cl.[7] ..... A01H 5/00

(52) U.S. Cl. ..... Plt./263; Plt./259

(58) Field of Search ..... Plt./263, 259

(56) References Cited

U.S. PATENT DOCUMENTS

PP11,122 P * 11/1999 Bovio ..... Plt./263

* cited by examiner

*Primary Examiner*—Wendy C. Haas
(74) *Attorney, Agent, or Firm*—Penny J. Aguirre

(57) ABSTRACT

A spotted dead nettle cultivar named 'Purple Dragon', characterized by silver and green variegated leaves and unique in having rich purple colored flowers borne in spring through fall.

8 Drawing Sheets

Botanical classification: *Lamium maculatum.*
Cultivar designation: 'Purple Dragon'.

BACKGROUND OF THE INVENTION

The present invention, 'Purple Dragon', originated in Whitefall, Mich., as a naturally occurring branch sport (mutation) from the unpatented cultivar *Lamium maculatum* 'White Nancy', which has similar foliage but with white flowers.

The parent plant, *L. maculatum* 'White Nancy' was growing in a nursery setting in a 4 inch size container. The inventor noticed the branch sport mutation (containing deep purple flowers) and later named it 'Purple Dragon'.

The cultivar 'White Nancy' typically displays silver centered, green edged leaves, and clear white flowers. 'Purple Dragon' differs principally in having deep purple colored flowers. It is similar to the parent cultivar in the habit (shape) of the plant.

The first successful asexual reproduction of 'Purple Dragon' was carried out by its discoverer. This propagation took place under controlled conditions in Spring Lake, Mich., on Sep. 1, 2000. The sport was excised, sectioned into 5 cuttings (bottom leaves removed on each), treated with 3000 ppm IBA, and rooted under intermittent mist in 3 inch containers over a period of two weeks. Five cuttings rooted and were later transplanted into 1 gallon size nursery containers for evaluation.

SUMMARY OF THE INVENTION

Once the plants in 1 gallon containers matured (after six months in the greenhouse as is typical for cultivars of this species), the plants were transplanted to growing beds for further evaluation. After observing them in the growing beds, the previously noted unique flower color continued to be observed. The plant has since spread and matured and has flowered repeatedly, each time displaying rich purple flowers. The overall habit of the plants was similar to the parent cultivar. Mature plants reach approximately 6 inches tall (measured from soil to top of plane of inflorescences).

Mature plants display a width of approximately 3 feet across.

BRIEF DESCRIPTION OF THE DRAWINGS

The accompanying photographic illustrations show typical foliage of the cultivar and the closest known comparison cultivars, with color being as accurate as possible with renditions of this type. The photographs were taken at 1 P.M. on Mar. 10, 2001 under partly sunny conditions, in Spring Lake, Mich. The film used was Kodak Gold ISO 100 exposed for 1/250 second at F4 using no filters.

FIG. # 1 is a perspective view of *L. maculatum* 'Purple Dragon',

Figure 1:
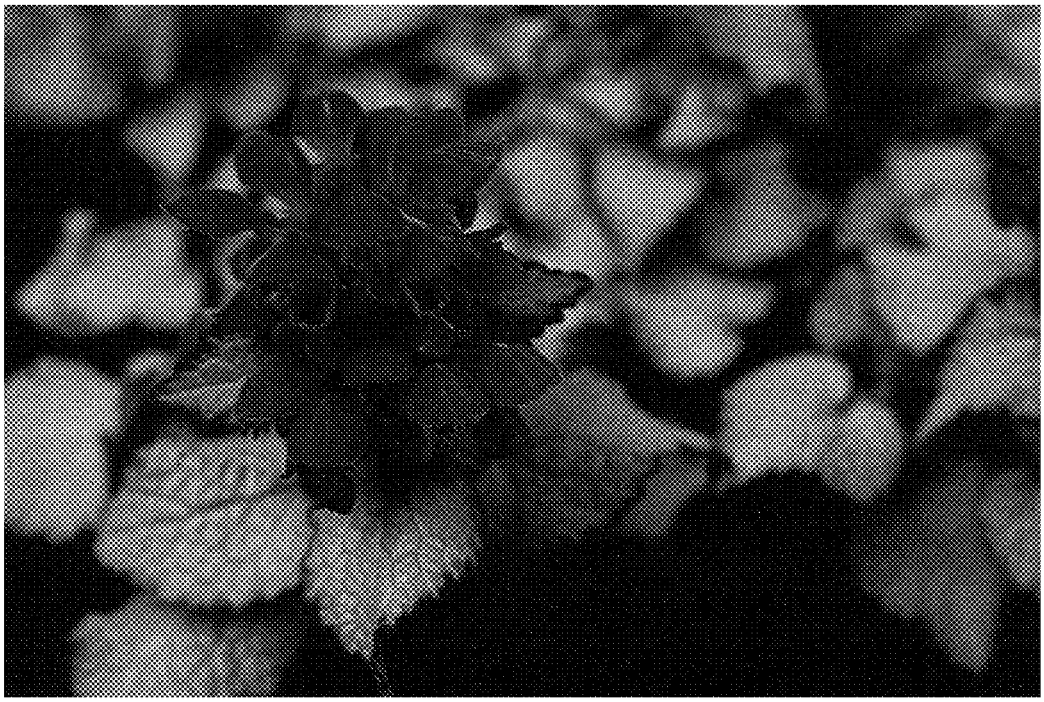
Figure 2:
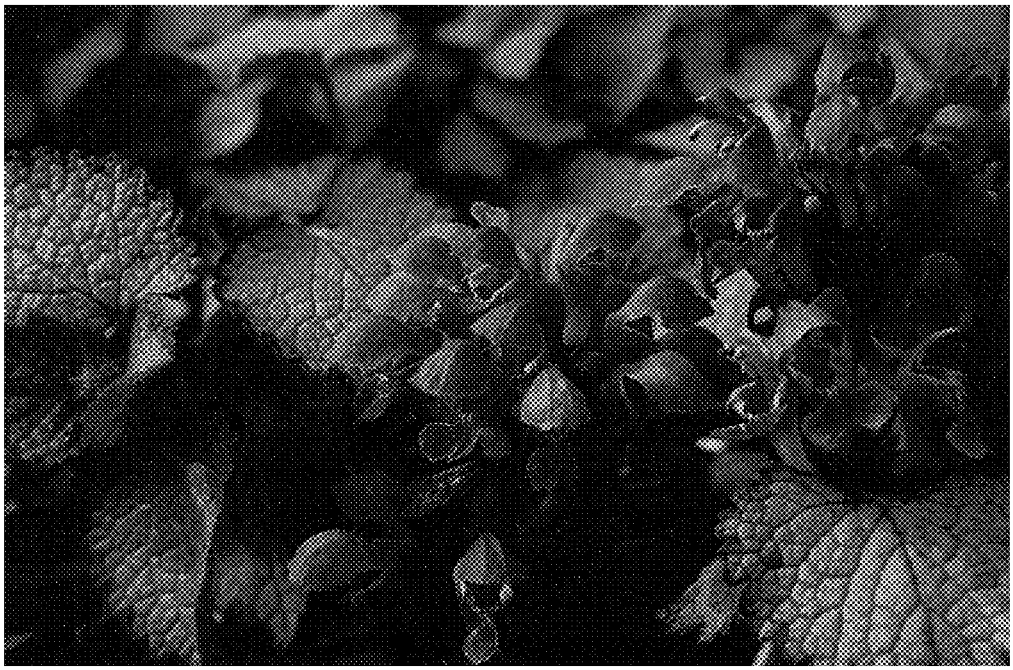
Figure 3:
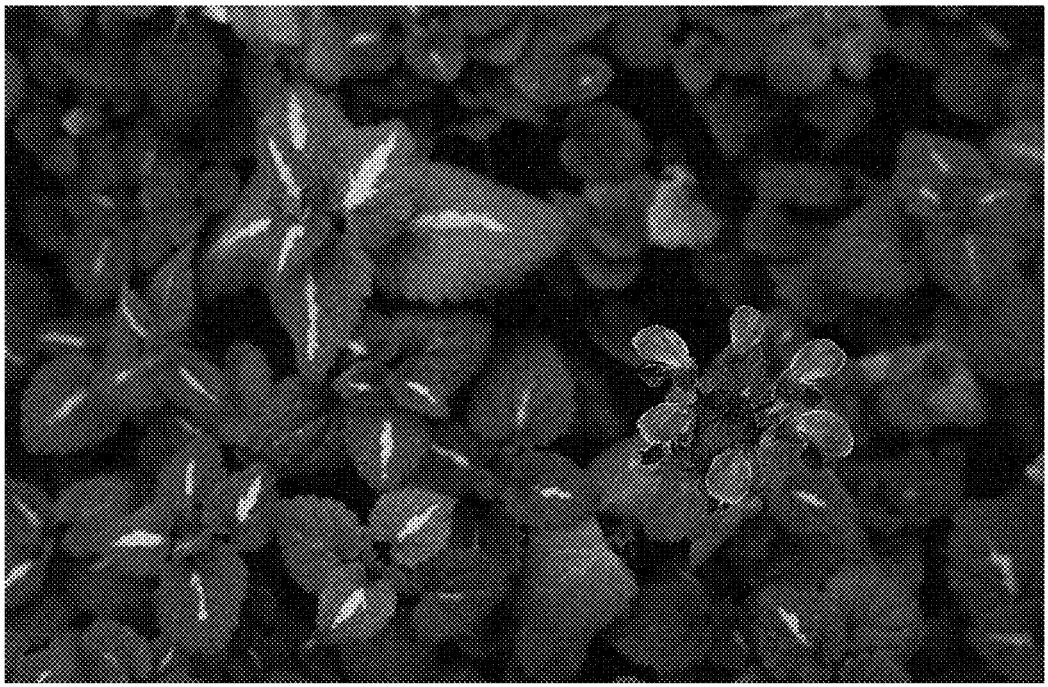
Figure 4:
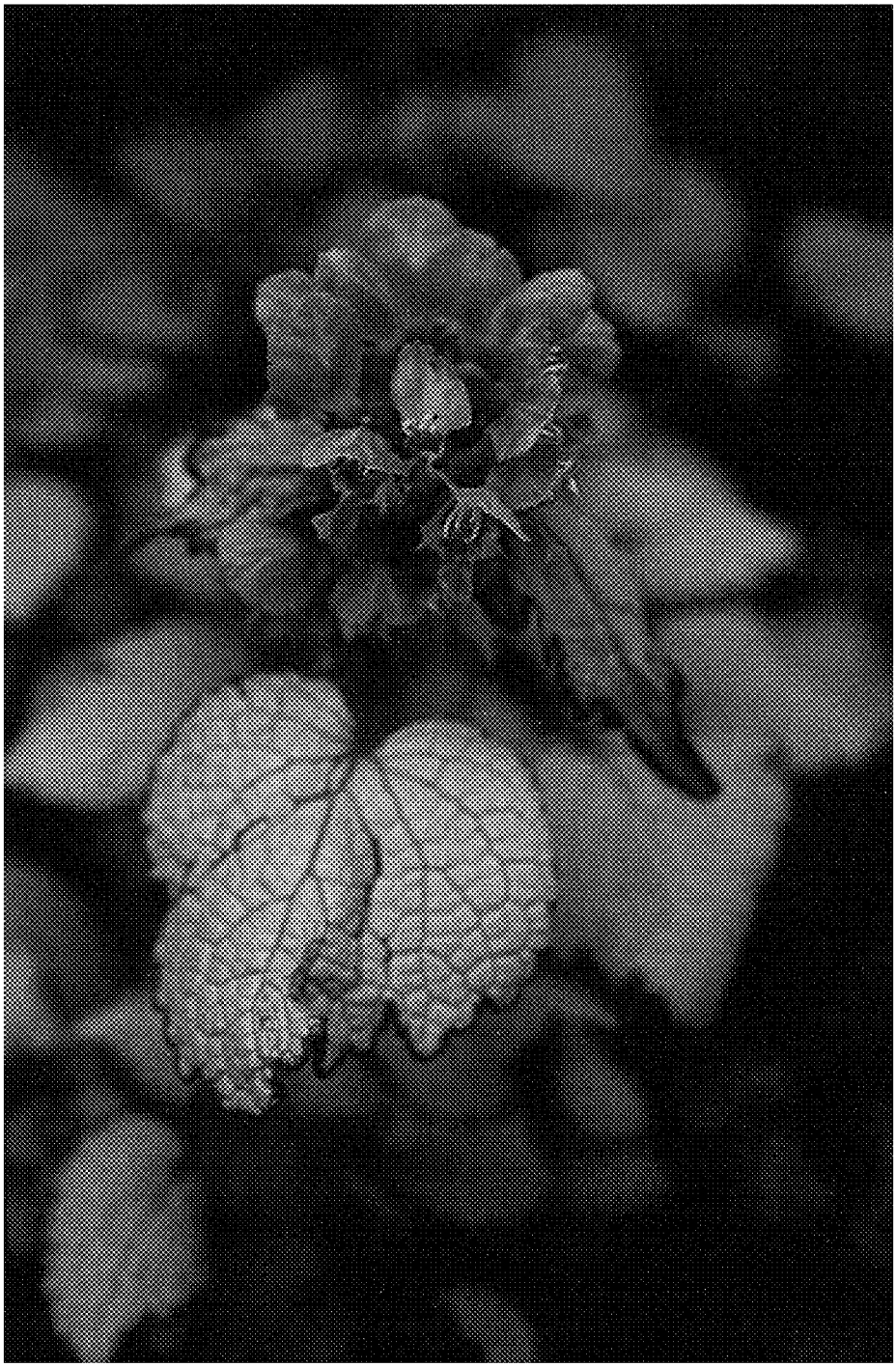
Figure 5:
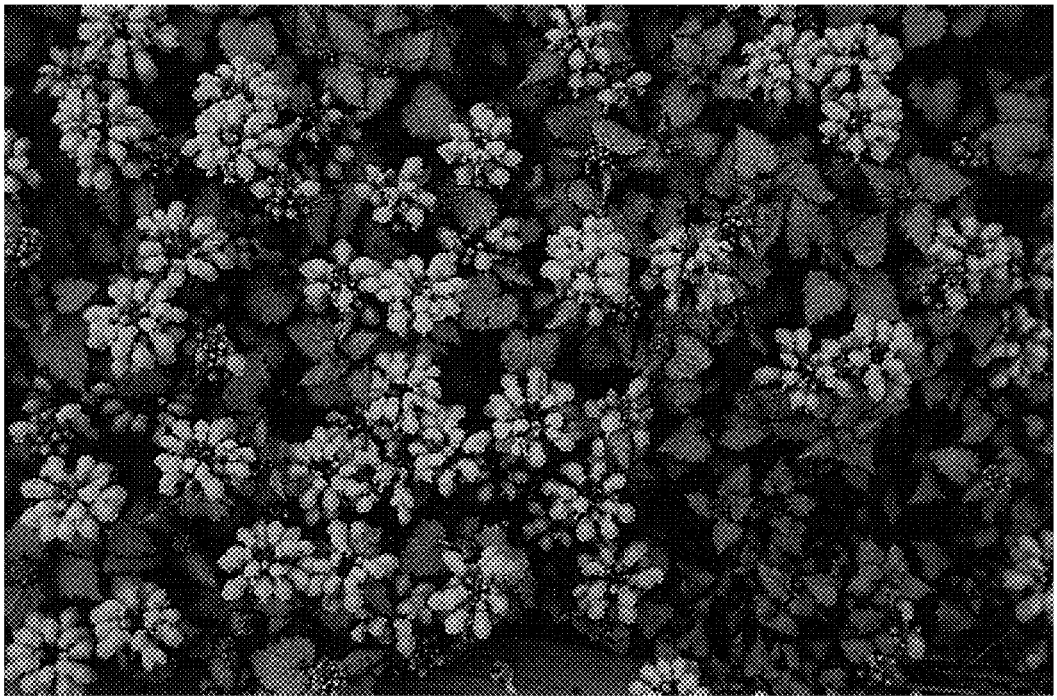
Figure 6:
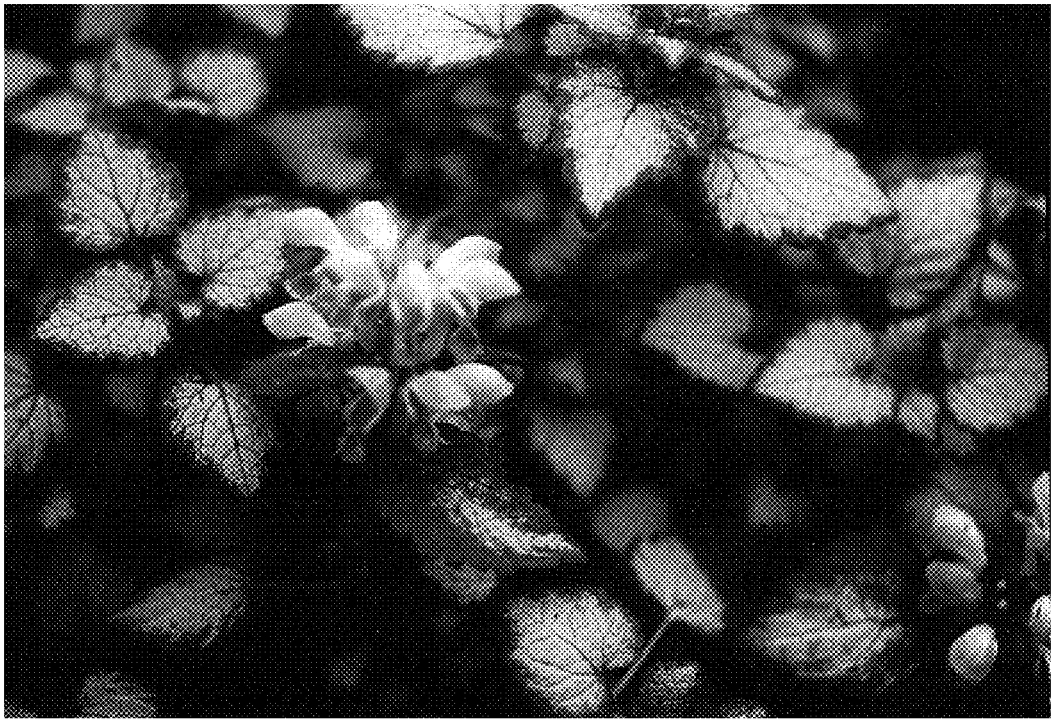
Figure 7:
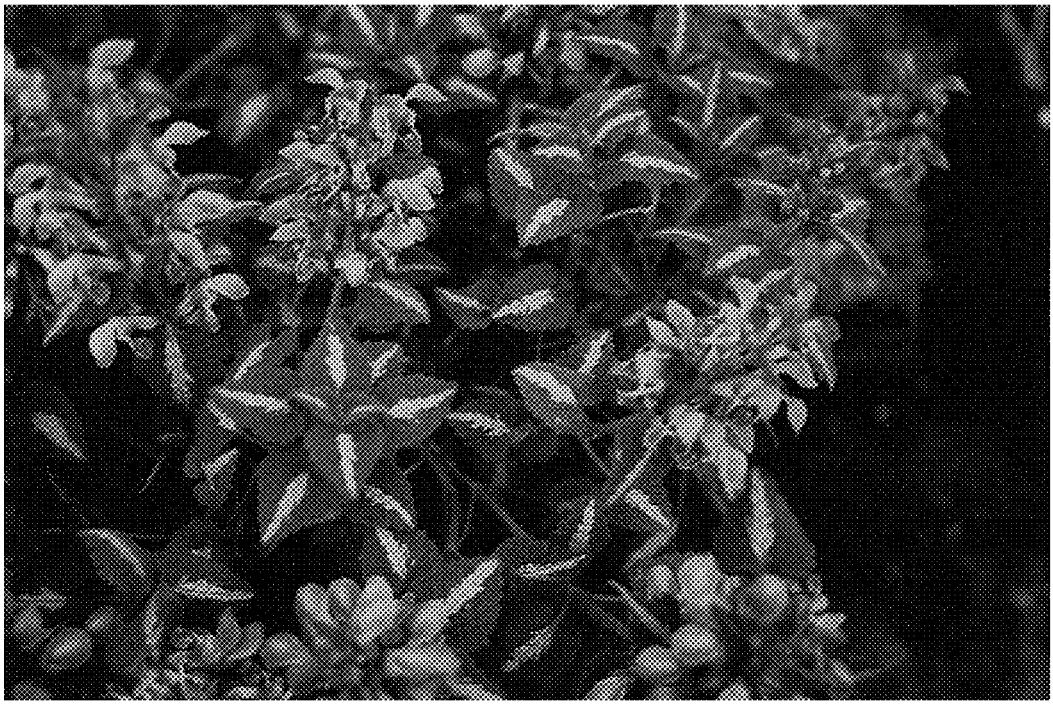
Figure 8:
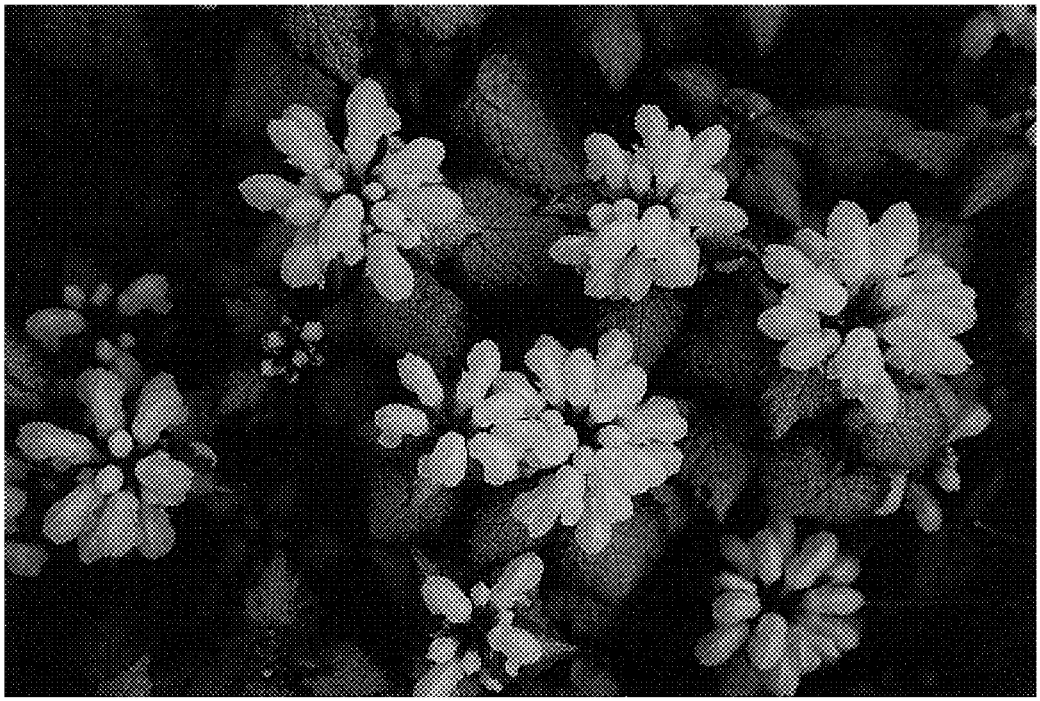

FIG. # 2 is a perspective view of *L. maculatum* 'Beacon Silver' (unpatented), FIG. # 3 is a perspective view of *L. maculatum* 'Chequers' (unpatented), FIG. # 4 is a perspective view of *L. maculatum* 'Orchid Frost' (U.S. Plant Pat. No. 11,122), FIG. # 5 is a perspective view of *L. maculatum* 'Pink Pewter' (unpatented), FIG. # 6 is a perspective view of *L. maculatum* 'Red Nancy' (unpatented), FIG. # 7 is a combined photo of *L. maculatum* 'Shell Pink' (unpatented), FIG. # 8 is a perspective view of *L. maculatum* 'White Nancy' (unpatented).

DETAILED BOTANICAL DESCRIPTION OF THE PLANT

'Purple Dragon' has not been observed under all possible environmental conditions, and the phenotype may vary significantly with variations in environment, such as temperature, light intensity and day length. The following observations, measurements, and comparisons describe this plant as grown in Spring Lake, Mich. when field grown (outdoors without cover) in conditions that approximate those generally used in commercial practice.

The following traits have been repeatedly observed and are determined to be the basic characteristics of 'Purple Dragon', which in combination distinguish this deed nettle as a new and distinct cultivar. The plant described were 3 years old and grown in the ground in full sun conditions in Spring Lake, Mich. The color codes correspond to The Royal Horticultural Society Colour Chart. The following description is based upon a 3-year old plant that is mature in every respect.

1. Stems of this cultivar arise at acute angles to the growing medium. As they elongate their weight causes them to droop over and sprawl horizontally—usually contacting the growing medium and rooting into the soil. Typically they reach 12 or more inches in length and often produce branches at their nodes.
2. Typical stems are herbaceous and are uniformly colored grayed-purple 184-A. The stems are square in cross section and 3/16 inch across.
3. Internodes range in length from 3/4 to 2½ inches. The nodes are 3/16 inch across and often sprout roots after a few weeks of contact with the growing medium. Thereafter, the plants generate a pair of new shoots from the buds on the distal end of the nodes.
4. Evergreen foliage is simple and arranged in opposite pairs. In youth, the foliage is ovate in outline, crenate edged, and colored either light green 145-A (about 25 percent of the new leaves are colored this way), or bicolored with the same coloration as the mature leaves (see #5 below).
5. Mature leaves are cordate, crenate, or crenate-dentate margined. Ranging from 2 inches long by 1¼ to 1½ inches wide, they are attached by 3/4–1¼ inch long light green petioles 135-D. Hair covered, they are somewhat velvety to the touch. Each is flat with obtuse apices.
6. The midribs are not prominent and are only slightly recessed into the blade. Colored medium green 143-A, they give rise to a network of secondary and tertiary veins of the same color.
7. Adult leaves are bicolored. The center is colored gray-green 192-C, and the leaf edge green 141-B. The leaf edge surrounds the entire leaf blade and is typically 1/8 inch wide.
8. Bisexual flowers are arranged in 2 inch tall, 2 to 3 inch wide verticillasters (dense whorls) and are borne primarily during late spring (mid May in Spring Lake, Mich.) then throughout the summer and fall months extending well into fall (flowers usually are present during early November in Spring Lake, Mich.). Each whorl may produce up to 30 flowers, but not all at the same time. The flowers have a pungent (relatively unpleasant) scent, which is typical of this species and other cultivars of this species.
9. Individual flowers are bilabiate (typical of the mint family). The flowers are typically composed of five medium green 143-A, linear, divergent, lobed calyzes. Each corolla is approximately 8/10 inch long by 7/16 inch wide, two-lipped, upper lip hooded, lower lip 3-lobed.
10. The funnel-like base of each corolla is colored white 155-D. The upper lip is purple violet 81-C on the inside and purple violet 80-A on its outside. The midrib of the upper lip is white 155-B, ½ inch long, 1/32 inch wide, and divided distally into two thin forks. The lateral lower lips are colored purple 78-A on all sides. The central lower lip is colored purple 77-A on both sides.
11. The fruit, grouped in fours, is unnoticeable with casual observation. Each is a tiny 1/8 inch long, 1/16 inch wide, green 135-D nutlet.
12. The cultivar 'Purple Dragon' displays no unique disease resistance or cold hardiness. Like the species and other cultivars of the species, it is hardy in USDA Zone 3.

Other related cultivars of spotted dead nettle are:

'Beacon Silver' (unpatented), with flowers somewhat smaller 3/4 inch long by 7/16 inch wide, colored red-purple 68-A on the outside of the upper lip of the corolla, and leaves with similar variegation and coloring (to 'Purple Dragon').

'Chequers' (unpatented), with rose-pink flowers and substantially different leaves (than 'Purple Dragon') which are smaller (3/4 inch long by 3/4 inch wide) and centered grayed-green 193-D with a broad 3/8 inch wide dark green 137-A margin.

'Orchid Frost' (U.S. Plant Pat. No. 11,122), with violet colored flowers, the upper lip violet 84-C on the inside and violet 84-A on its outside.

'Pink Pewter' (unpatented), with 3/4 inch flowers that are colored red-purple 73-D. Its leaves are typically 1¼ inch long by 5/8 inch wide (smaller than 'Purple Dragon'). Colored gray-green 192-B in their center, they are surrounded with a thin, irregular 1/16 to 1/5 inch wide margin of dark green 137-B.

'Red Nancy' (unpatented), has 3/4 inch long flowers that are colored violet 84-B. Its leaves are typically 1 inch long by 3/4 inch wide. Colored grayed-green 192-B in their center, they are surrounded with a thin, 1/10 inch wide margin of dark green 137-D.

'Shell Pink' (unpatented), with 3/4 inch long flowers that are colored pink 62-C, and leaves smaller, to 1 inch long and 1 inch wide, that are centered grayed-green 192-A with a broad ½ inch wide margin of dark green 137-B.

'White Nancy' (unpatented), with white 155-D flowers measuring 3/4 inch long by 7/16 inch wide, and leaves with similar variegation, size, and coloring (to 'Purple Dragon').

I claim:

1. A new and distinct cultivar of *Lamium maculatum* plant, 'Purple Dragon' as herein illustrated and described.

* * * * *